(12) United States Patent
Hawkins et al.

(10) Patent No.: US 6,339,652 B1
(45) Date of Patent: *Jan. 15, 2002

(54) SOURCE-ASSISTED ATTENUATION CORRECTION FOR EMISSION COMPUTED TOMOGRAPHY

(75) Inventors: William G. Hawkins, Shaker Heights; Daniel Gagnon, Twinsburg, both of OH (US)

(73) Assignee: Picker International, Inc., Highland Heights, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/437,784

(22) Filed: Nov. 10, 1999

Related U.S. Application Data

(63) Continuation-in-part of application No. 09/198,787, filed on Nov. 24, 1998.

(51) Int. Cl.$^7$ .................................................. G06K 9/00

(52) U.S. Cl. ....................................... 382/131; 250/455

(58) Field of Search .................... 382/131; 250/363.04, 250/455; 378/4; 364/414

(56) References Cited

U.S. PATENT DOCUMENTS

| | | | | |
|---|---|---|---|---|
| 4,672,648 A | * | 6/1987 | Mattson et al. ................. | 378/4 |
| 5,210,421 A | * | 5/1993 | Gullberg et al. ....... | 250/363.04 |
| 5,338,936 A | | 8/1994 | Gullberg et al. | |
| 5,479,021 A | * | 12/1995 | Morgan et al. ........ | 250/363.04 |
| 5,559,335 A | * | 9/1996 | Zeng et al. ............ | 250/363.04 |
| 5,814,817 A | * | 9/1999 | Guillemaud et al. ... | 250/363.04 |
| 6,008,493 A | * | 12/1999 | Shao et al. ............ | 250/363.04 |

OTHER PUBLICATIONS

Y. Censor, et al., "A New Approach to the Emission Computerized Tomography Problem: Simultaneous Calculation of Attenuation and Activity Coefficients," *IEEE Trans. On Nucl. Sci.*, vol. NS–26, No. 2, pp. 2775–2779, Apr. 1979.

K. Lange, et al., "A Theoretical Study of Some Maximum Likelihood Algorithms for Emission and Transmission Tomography," *IEEE Trans. on Medical Imaging*, vol. MI–6, No. 2, pp. 106–114, Jun. 1987.

C. H. Tung, et al., "Non–Uniform Attenuation Correction Using Simultaneous Transmission and Emission Converging Tomography," pp. 2018–2022.

(List continued on next page.)

*Primary Examiner*—Joseph Mancuso
*Assistant Examiner*—Abolfazl Tabatabai
(74) *Attorney, Agent, or Firm*—Fay, Sharpe, Fagan, Minnich & McKee, LLP

(57) ABSTRACT

A method of ML-EM image reconstruction is provided for use in connection with a diagnostic imaging apparatus (10) that generates projection data. The method includes collecting projection data, including measured emission projection data and measured transmission projection data. Optionally, the measured transmission projection data is truncated. An initial emission map and attenuation map are assumed. The emission map and the attenuation map are iteratively updated. With each iteration, the emission map is recalculated by taking a previous emission map and adjusting it based upon: (i) the measured emission projection data; (ii) a reprojection of the previous emission map which is carried out with a multi-dimensional projection model; and, (iii) a reprojection of the attenuation map. As well, with each iteration, the attenuation map is recalculated by taking a previous attenuation map and adjusting it based upon: (i) the measured emission projection data; (ii) a reprojection of the previous emission map which is carried out with the multi-dimensional projection model; and (iii) measured transmission projection data.

21 Claims, 7 Drawing Sheets

OTHER PUBLICATIONS

K. Lange, et al., "EM Reconstruction Algorithms for Emission and Transmission Tomography," *Journal of Computer Assisted Tomography*, vol. 8, No. 2, pp. 306–316, 1984.

C. H. Tung, et al., "A Simulation of Emission and Transmission Noise Propagation in Cardiac SPECT Imaging with Nonuniform Attenuation Correction," *Medical Physics*, vol. 21, No. 10, pp. 1565–1576, Oct. 1994.

A. Krol, et al., "An EM Algorithm for Estimating SPECT Emission and Transmission Parameters from Emission Data Only."

* cited by examiner

SOURCE-ASSISTED ATTENUATION CORRECTION FOR EMISSION COMPUTED TOMOGRAPHY

This application is a continuation-in-part of co-pending U.S. patent application Ser. No. 09/198,787 filed Nov. 24, 1998.

BACKGROUND OF THE INVENTION

The present invention relates to the art of diagnostic medical imaging. It finds particular application in conjunction with single photon emission computed tomography (SPECT) and nuclear cameras, and will be described with particular reference thereto. However, it is to be appreciated that the present invention is also amenable to other like applications including, but not limited to, positron emission tomography (PET) and ultrasound tomography.

Attenuation correction is now an integral part of nuclear medicine image reconstruction. Several techniques have been introduced over the years, ranging from simple analytical filters to elaborate transmission devices, to obtain an object--dependent attenuation map. Often, in analytical correction, assumptions are made that are too restrictive to be realistic. Object-dependent attenuation correction based on emission data only is an attractive and theoretically sound alternative, but not ready for large scale utilization. Finally, techniques based on an attenuation map constructed from measured transmission projection data, while a popular approach, suffer from very poor statistical quality. Moreover, current techniques for reconstructing the emission data are sensitive to this noise. Moreover, the collected transmission projection data is often truncated.

The approaches presented herein are a departure from previously available techniques. In order to appreciate the difference, it is helpful to examine previous techniques.

It is usually recognized that iterative methods lend themselves easily to the introduction of additional correction factors such as attenuation. With reference to FIG. 1, the basic concept behind iterative methods, such as maximum likelihood expectation maximization (ML-EM) reconstruction, is to find the object (i.e., image or emission map) for which a mathematical projection produces results comparable to the set of measured emission projections. The ML-EM reconstruction algorithm is one such engine that allows the image to be found in an efficient manner. From an initial guess or assumption, a set of projections is artificially created by a projector employing a projection model. These projections are then compared to the "real" or measured set. When certain conditions are met (i.e., when the projections of the emission map are sufficiently close to the measured emission projections), the iterative process stops and the current image is the best possible representation of the object, otherwise, the initial guess is updated and a new set of projections produced. Clearly, the projection model employed is an important part of the projection operation. However, an accurate projection model can be complex and detailed.

With reference to FIG. 2, one way to improve the "realism" of the projection model or the update operations is to include a priori information, i.e., what is already known about the object (e.g., its contour, texture, and so forth). In general, this is a powerful tool that offers dramatic improvement of the reconstruction. One caveat is, however, that this information needs to be real. In other words, if a priori information is true or accurate, it helps the reconstruction. On the other hand, inaccuracy tends to inappropriately bias the reconstruction or otherwise introduce unwanted artifacts. Moreover, in practice, it is difficult to find non-trivial characteristics of the object to be imaged that are always accurate.

With reference to FIG. 3, the attenuation map is certainly one element that can help the reconstruction. Information pertaining to attenuation characteristics can be generated artificially for simple situations (e.g, uniform attenuation, symmetrical attenuation, etc.). In general, however, inaccuracies can be introduced by suggesting attenuation features that are not true and/or not object specific.

With reference to FIG. 4, it is significantly more advantageous when the attenuation map is constructed for each object and used directly in the reconstruction. Often, the attenuation map is derived from measured transmission projection data. This is the basis of most of the modern non-uniform attenuation correction devices. However, the problem with this approach is statistics. Typically, in order to define a useful and usable attenuation map, many counts are needed. In practice, however, the definition of the attenuation map is count-limited, and the inherent noise associated with it is transported into the reconstruction of the emission map. Another problem is that often the transmission projection data used to derive the attenuation map is truncated thereby resulting in a degraded attenuation map. In other words, a poor attenuation map can actually degrade the image it aims at improving because of a lack of counts and/or a truncated transmission data set.

These limitations in the acquisition of the measured attenuation maps have provided the motivation for investigation into different techniques. It is generally known that the emission data contains information from which theoretically the attenuation map could be reconstructed. Such reconstruction methods are referred to as sourceless. In fact, each point in the object can be considered as a transmission source, and the observed intensity at any given point on the detector can be compared with the expected intensity without attenuation. Unfortunately, due to limitations, such as the limited number of counts in the emission map, the relationship between the emission and attenuation maps can only partially be established. Moreover, there is an intrinsic inability of the process to differentiate between a low activity, low attenuation condition and a high activity, high attenuation condition.

Yet another drawback of previous techniques is that they tend to employ only a linear projection model. That is to say, they merely account for those events that lie along a singular path or line from the detection bin to the activity. Such projection models are not adapted to account for scatter or collimator resolution which may allow a particular detector bin to detect photons from off-line sources.

The present invention contemplates a new and improved technique for providing attenuation correction in emission computed tomography which overcomes the above-referenced problems and others.

SUMMARY OF THE INVENTION

In accordance with one aspect of the present invention, a method of ML-EM image reconstruction is provided for use in connection with a diagnostic imaging apparatus that generates projection data. The method includes collecting projection data including measured emission projection data and measured transmission projection data. Optionally, the measured transmission projection data is truncated. Initial emission and attenuation maps are assumed and iteratively updated. With each iteration, the emission map is recalculated by taking a previous emission map and adjusting it based upon: (i) the measured emission projection data; (ii) a reprojection of the previous emission map which is carried out with a multi-dimensional projection model; and, (iii) a reprojection of the attenuation map. Also, with each iteration, the attenuation map is recalculated by taking a previous attenuation map and adjusting it based upon: (i) the measured emission projection data; (ii) the reprojection of the previous emission map which is carried out with the multi-dimensional projection model; and, (iii) the measured transmission projection data.

In accordance with another aspect of the present invention, a medical diagnostic imaging apparatus for reconstructing image representations of a subject being examined therewith is provided. It includes a emission memory which stores measured emission projection data from the subject. A transmission memory stores measured transmission projection data from the subject. Optionally, the measured transmission projection data is truncated. An image memory stores emission maps, and an attenuation map memory stores attenuation maps. A first projector generates emission map projections via forward projection of the emission maps from the image memory. Likewise, a second projector generates attenuation map projections via forward projection of the attenuation maps from the attenuation map memory. The first and second projectors use first and second multi-dimensional projection models, respectively. A first data processor samples the emission memory, and the first projector, and in accordance therewith updates the attenuation maps stored in the attenuation map memory. A second data processor samples the emission memory, the first projector, and the second projector, and in accordance therewith updates the emission maps stored in the image memory. Finally, a human-viewable display renders reconstructed image representations of the subject from the emission maps.

In accordance with another aspect of the present invention, a method of reconstructing an image is provided for use in connection with a nuclear imaging apparatus. The method includes collecting emission projection data and truncated transmission data. Thereafter, an attenuation map is updated in accordance with the collected transmission projection data, the collected emission projection data, and a reprojection of an emission map. Likewise, the emission map is updated in accordance with the collected emission map, the reprojection of the preceding emission map, and a reprojection of the attenuation map.

One advantage of the present invention is improved attenuation maps for ML-EM reconstruction.

Another advantage of the present invention is multi-dimensional projection modeling which more accurately approximates actual conditions.

Yet another advantage of the present invention is that there is less likelihood of noise being introduced into the final reconstruction via the attenuation map.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
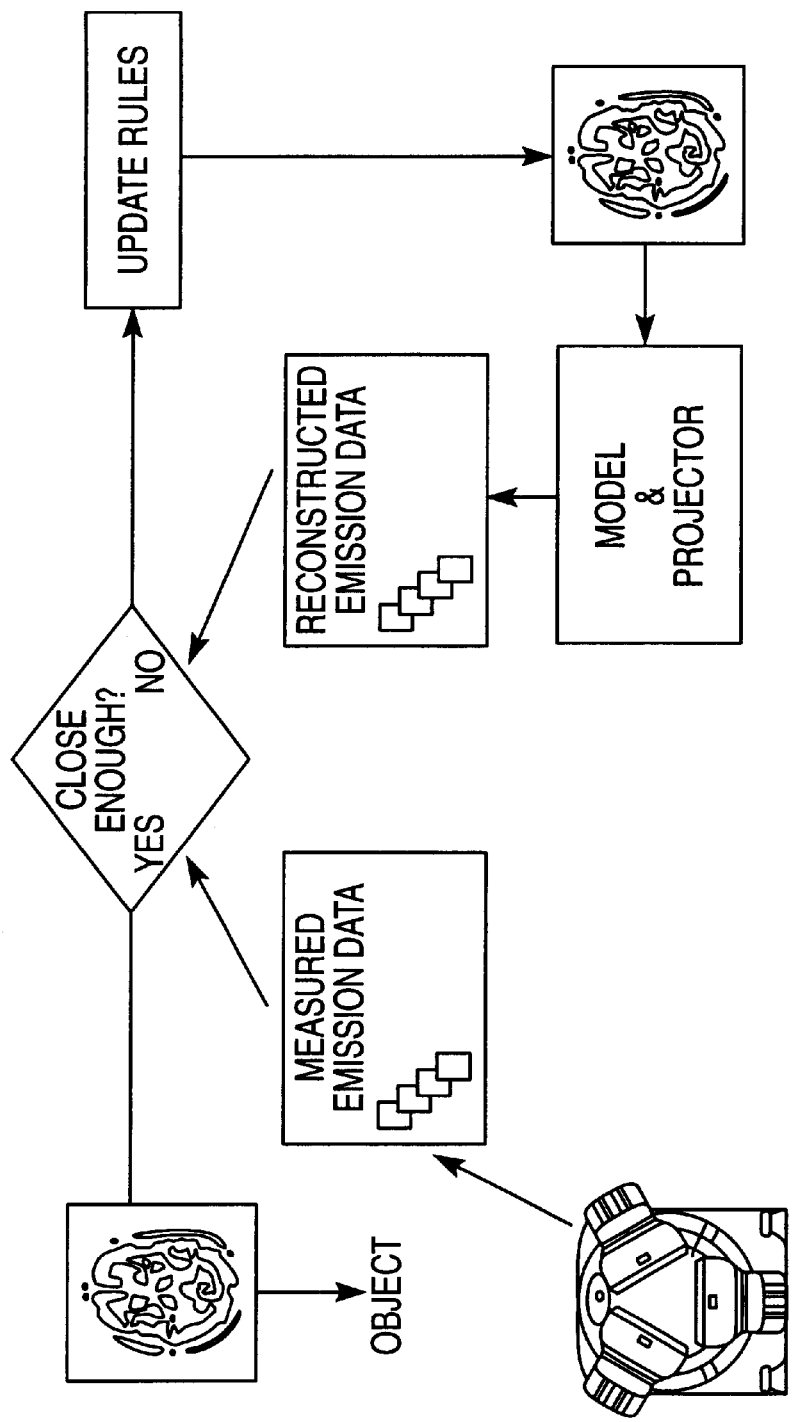
FIG. 1 is a flow diagram illustrating the operation of a typical ML-EM reconstruction method in accordance with prior art techniques.
Figure 2:
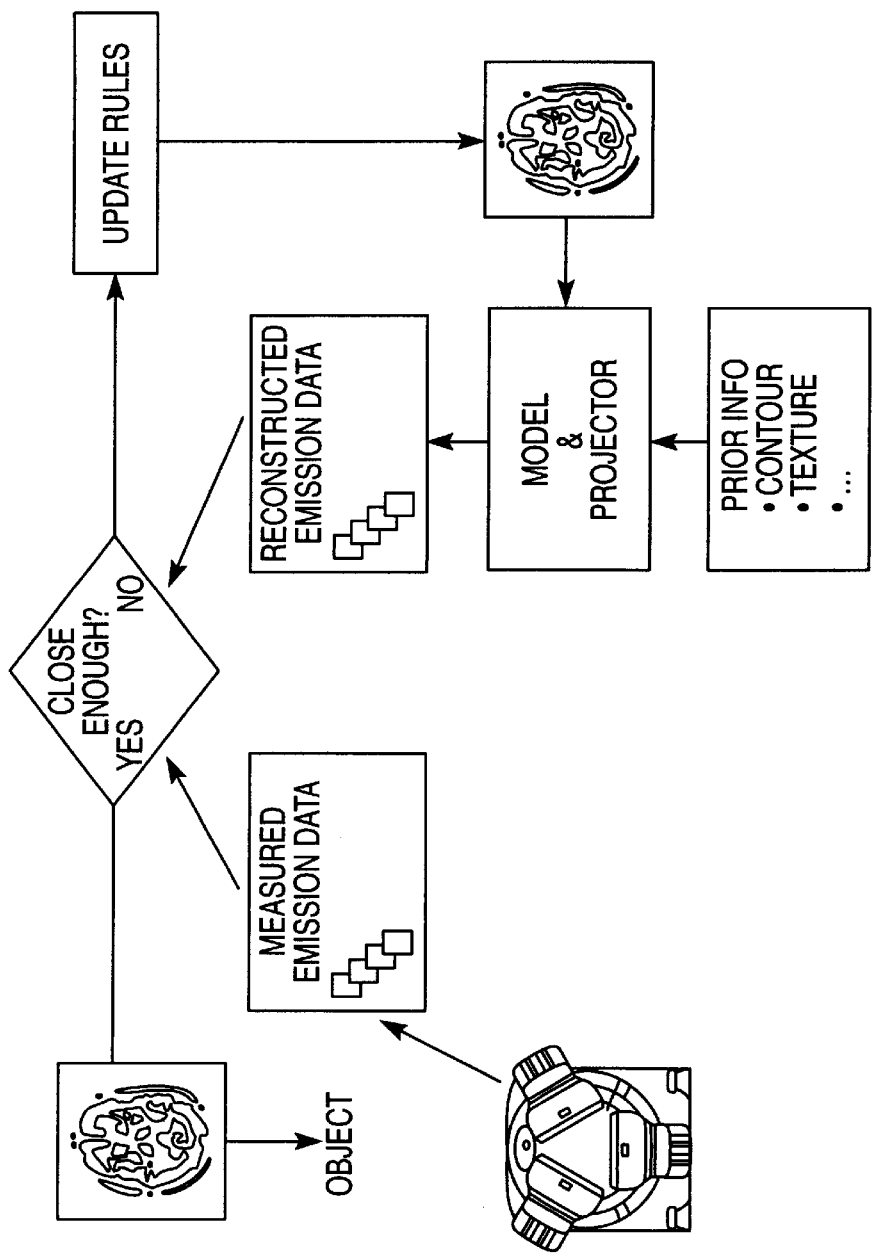
FIG. 2 is a flow diagram illustrating the operation of a typical ML-EM reconstruction method employing a priori information in accordance with prior art techniques.
Figure 3:
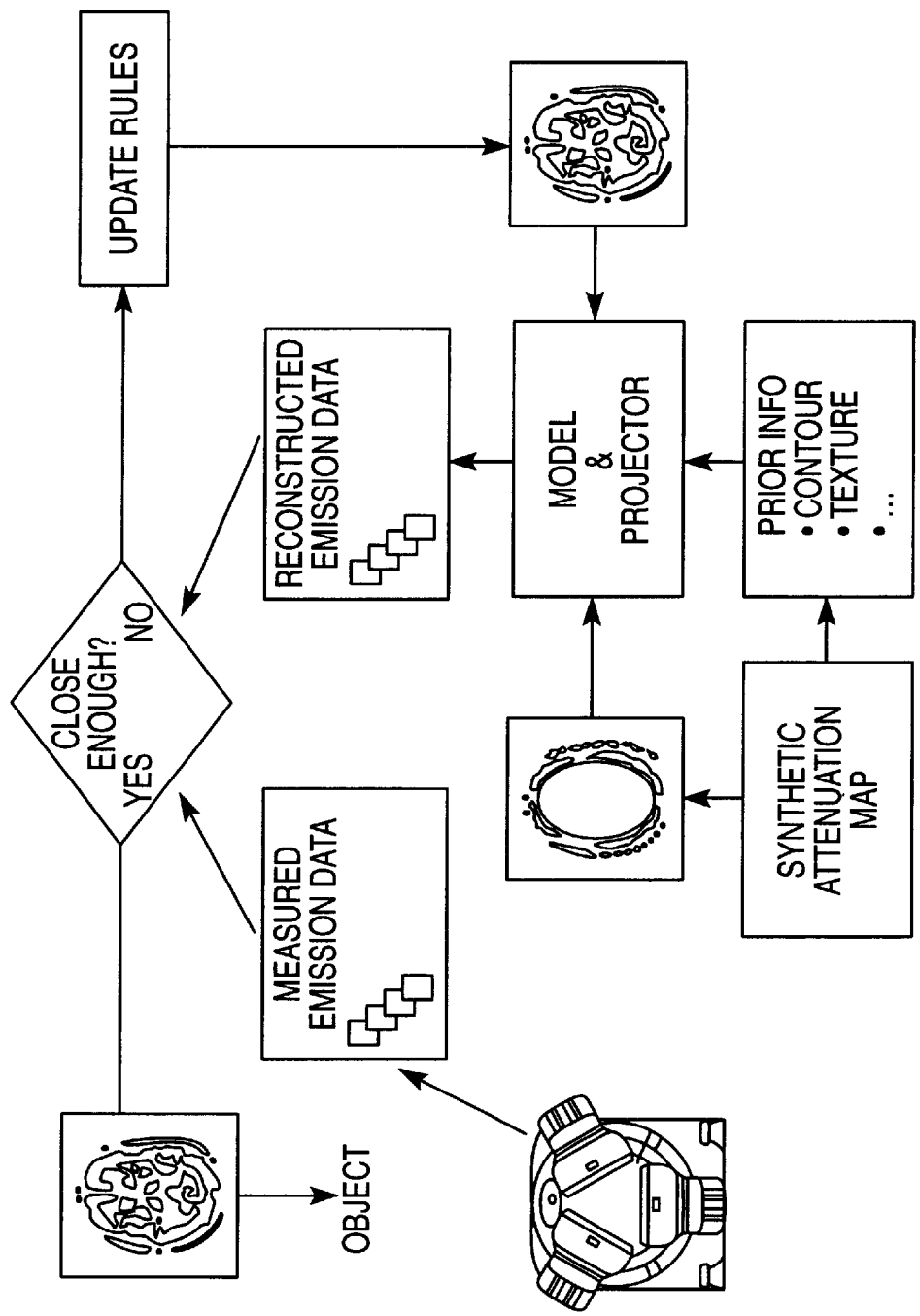
FIG. 3 is a flow diagram illustrating the operation of a typical ML-EM reconstruction method employing an artificially generated attenuation map in accordance with prior art techniques.
Figure 4:
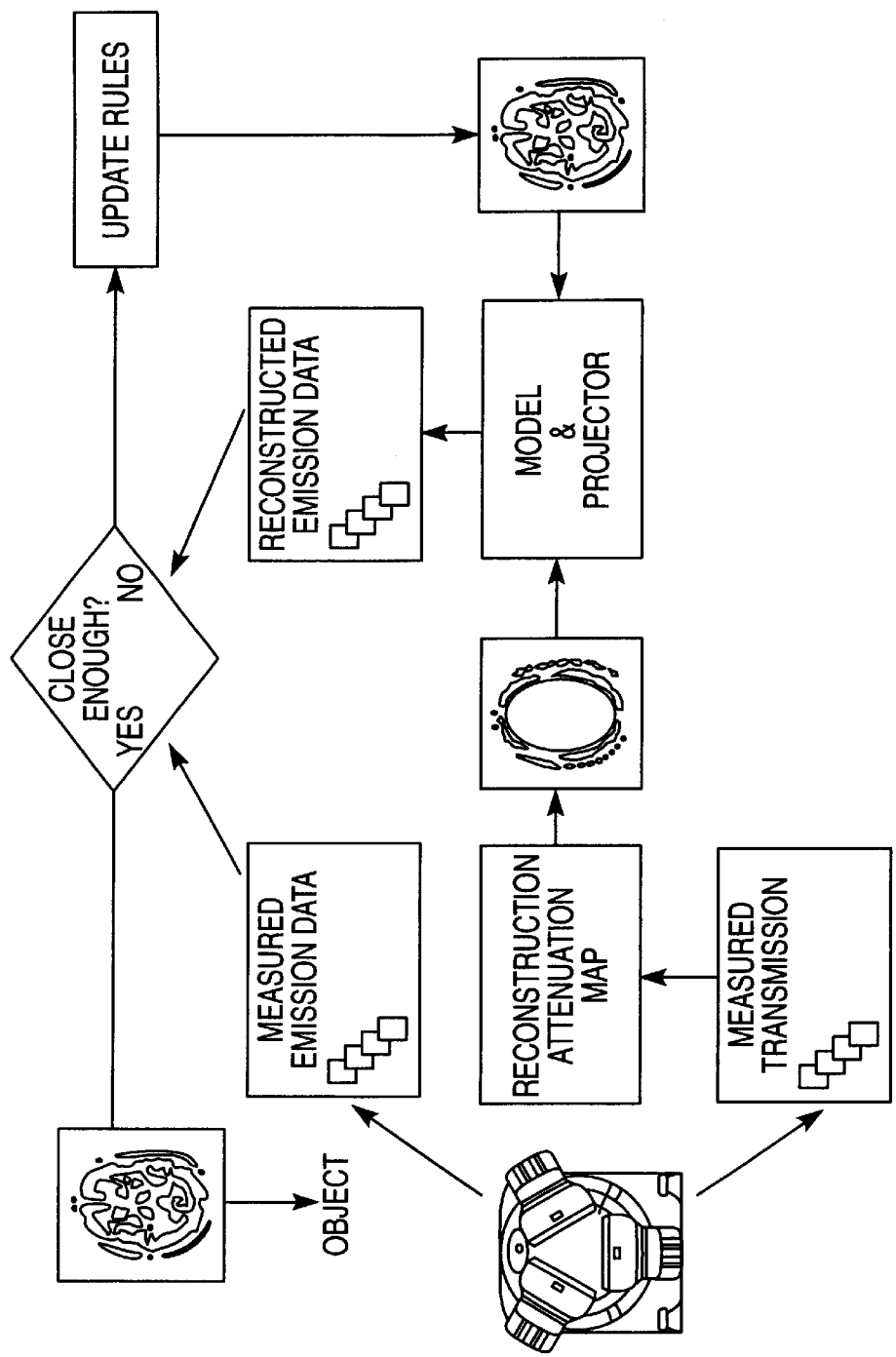
FIG. 4 is a flow diagram illustrating the operation of a typical ML-EM reconstruction method employing an attenuation map derived from measured transmission projection data in accordance with prior art techniques.
Figure 5:
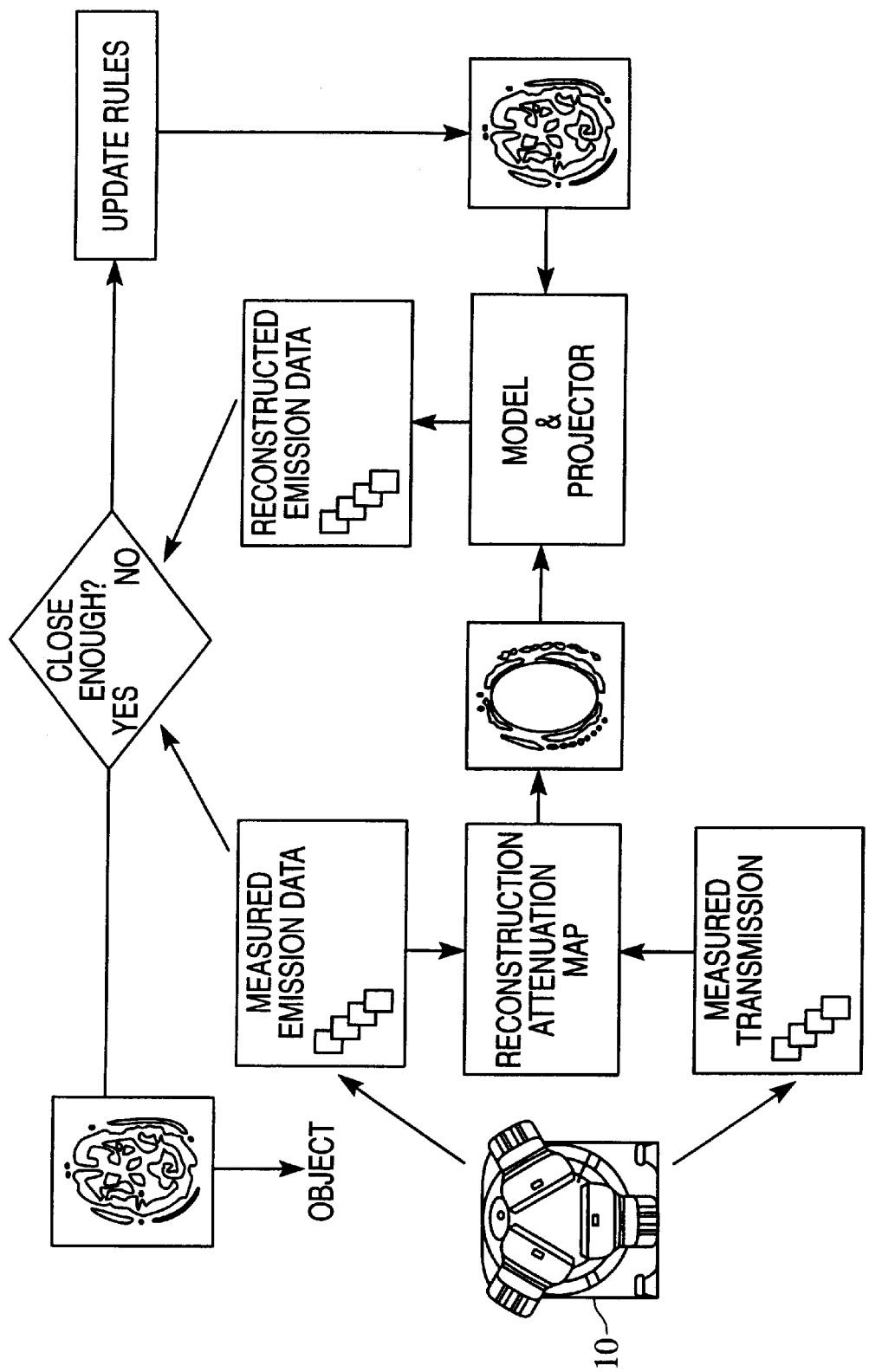
FIG. 5 is a flow diagram illustrating source-assisted ML-EM reconstruction in accordance with aspects of the present invention.

With reference to FIG. 5, the basic flow of a source-assisted ML-EM reconstruction in accordance with the present invention is illustrated. A medical diagnostic imaging apparatus 10 (described in greater detail below) generates emission and transmission projection data. Source-assisted attenuation correction combines the benefit of real transmission measurements with the stability of an analytical sourceless approach. In this approach, the measured transmission projection data, however statistically poor and/or truncated, is used to stabilize the analytical approach and force the attenuation map and the emission map to be independent. The transmission information and emission counts are combined to form an image of the attenuation map. The result is improved quality in the attenuation map, because the emission data is used to "assist" in its reconstruction. This, in turn, improves the reconstruction of the emission map in terms of quantitative accuracy. Moreover, in a preferred embodiment, multi-dimensional projection models provide a more accurate reconstruction.

The medical diagnostic imaging apparatus 10 is generally any nuclear medicine scanner that produces scintigraphic images, for example, SPECT scanners or PET scanners. An appropriate device is one that detects and records the spatial, temporal, and/or other characteristics of emitted photons.

Figure 6:
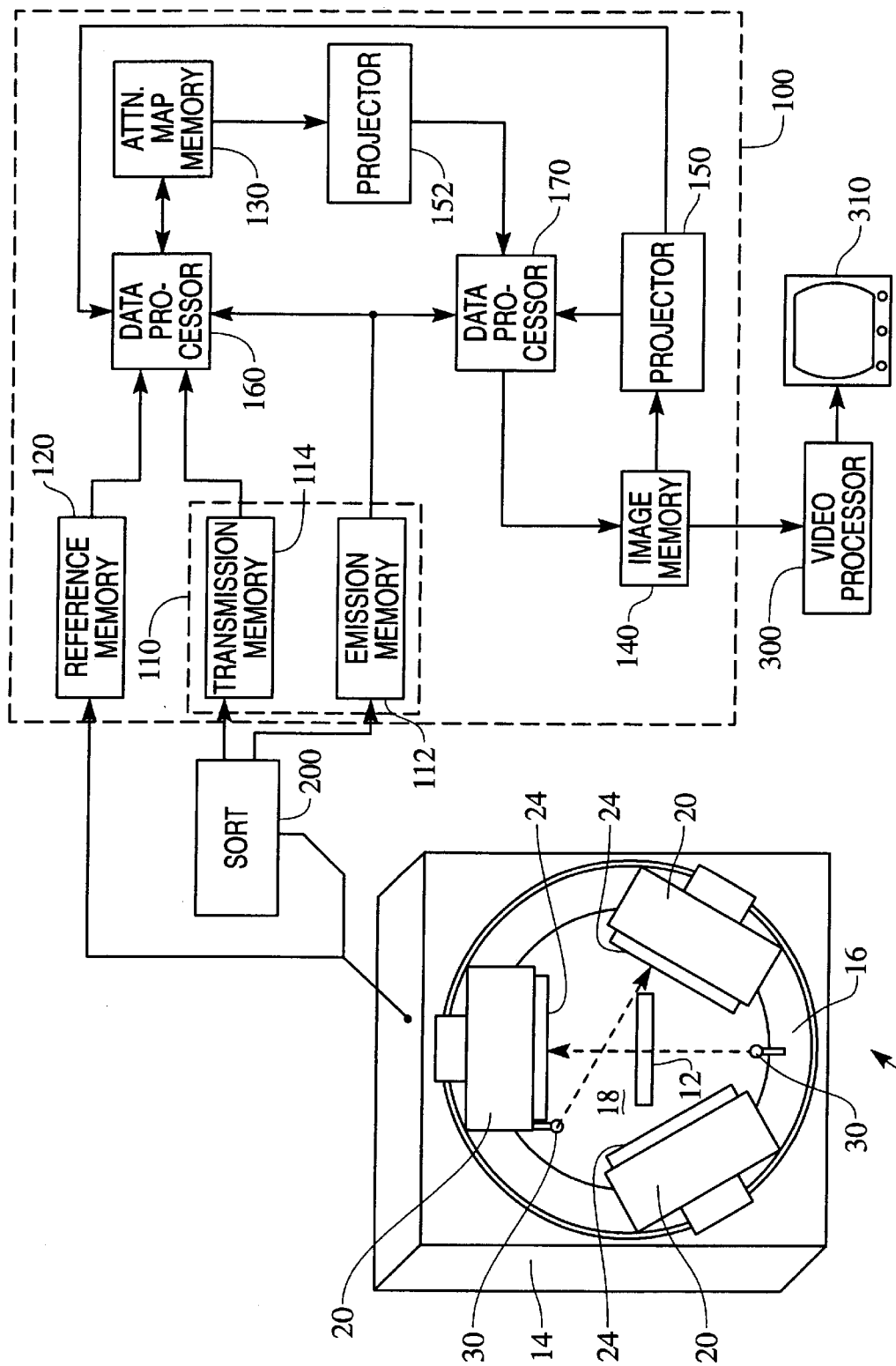
FIG. 6 is a diagrammatic illustration of a diagnostic nuclear imaging apparatus employing an image processor which carries out ML-EM reconstruction in accordance with aspects of the present invention; and, FIG. 7 is a graphical illustration showing the set of pixels employed in the reconstruction of SPECT data in accordance with aspects of the present invention.

More specifically, with reference to FIG. 6, in an exemplary embodiment, the diagnostic nuclear imaging apparatus or scanner 10 is a gamma camera or SPECT scanner including a subject support 12, such as a table or couch, which supports and positions a subject being examined and/or imaged, such as a phantom or patient, within a subject-receiving aperture 18. The subject is injected with one or more radiopharmaceutical or radioisotopes such that emission radiation is emitted therefrom. A first gantry 14 holds a rotating gantry 16 mounted thereto. The rotating gantry 16 defines the subject-receiving aperture 18. One or more detector heads 20 are adjustably mounted to the rotating gantry 16 with varying degrees of freedom of movement. Being mounted to the rotating gantry 16, the detector heads 20 rotate about the subject-receiving aperture 18 (and the subject when located therein) along with the rotation of the rotating gantry 16. In operation, the detector heads 20 are rotated or indexed around the subject to monitor radiation from a plurality of directions to obtain a plurality of different angular views.

Each of the detector heads 20 has a radiation-receiving face facing the subject-receiving aperture 18 that includes a scintillation crystal, such as a large doped sodium iodide crystal, that emits a flash of light or photons in response to incident radiation. An array of photomultiplier tubes receives the light and converts it into electrical signals. A resolver circuit resolves the x, y-coordinates of each flash of light and the energy of the incident radiation. That is to say, radiation strikes the scintillation crystal causing the scintillation crystal to scintillate, i.e., emit light photons in response to the radiation. The photons are directed toward the photomultiplier tubes. Relative outputs of the photomultiplier tubes are processed and corrected to generate an output signal indicative of (1) a position coordinate on the detector head at which each radiation event is received, and (2) an energy of each event. The energy is used to differentiate between various types of radiation such as multiple emission radiation sources, stray and secondary emission radiation, transmission radiation, and to eliminate noise. An image representation is defined by the radiation data received at each coordinate. The radiation data is then reconstructed into an image representation of the region of interest.

Optionally, the detector heads 20 include mechanical collimators 24 removably mounted on the radiation receiving faces of the detector heads 20. The collimators 24 preferably include an array or grid of lead or otherwise radiation-absorbent vanes which restrict the detector heads 20 from receiving radiation not traveling along selected rays in accordance with the data type being collected (i.e., parallel beam, fan beam, and/or cone beam). Alternately, for example, when operating in a coincidence mode, the collimators 24 may be omitted.

One or more radiation sources 30 are mounted across the subject-receiving aperture 18 from the detector heads 20. Optionally, they are mounted between the detector heads 20 or to the radiation receiving faces of opposing detector heads 20 such that transmission radiation from the radiation sources 30 is directed toward and received by corresponding detector heads 20 on an opposite side of the subject-receiving aperture 18. In a preferred embodiment, the collimators 24 employed on the detector heads 20, in effect, collimate the transmission radiation. That is to say, the collimators 24 restrict the detector heads 20 from receiving those portions of transmission radiation not traveling along rays normal (for parallel beam configurations) to the radiation receiving faces of the detector heads 20. Alternately, other collimation geometries are employed and/or the collimation may take place at the source.

In a preferred embodiment, the radiation sources 30 are moving point sources each traversing the length of the respective detector heads 20 to which they correspond. Alternately, line sources are employed such as, e.g., thin steel tubes filled with radionuclides and sealed at their ends. In other embodiments, the radiation sources 30 are bar sources, point sources, flat rectangular sources, disk sources, flood sources, a tube or vessel filled with radionuclides, or active radiation generators such as x-ray tubes. Alternately, one or more point sources of transmission radiation may be utilized.

The running of an imaging operation includes an iterative ML-EM reconstruction technique wherein emission projection data is reconstructed via an image processor 100 into an image representation of the distribution of radioactive material in the patient. Of course, the reconstruction technique implemented varies slightly in accordance with the types of radiation collected, the types of collimators used (i.e. fan, cone, parallel beam, and/or other modes), and the diagnostic imaging apparatus employed. In any case, emission radiation from the patient is received, for example, by the detector heads 20 of the SPECT scanner, and measured emission projection data is generated. The measured emission projection data normally contains inaccuracies caused by varying absorption or attenuation characteristics of the patient's anatomy. Preferably, a transmission scan is also performed such that transmission radiation from one or more of the transmission radiation sources 30 is also received, for example by the detector heads 20 of the SPECT scanner, and measured transmission projection data is generated. However, the measured transmission projection data is often noisy and/or truncated. A sorter 200 sorts the measured emission and transmission projection data on the basis of their relative energies. The data is stored in a measured projection view memory 110, more specifically, in a corresponding emission memory 112 and transmission memory 114.

Regarding the collected transmission projection data, a pre-scan blank run is performed to collect a baseline or reference with which to evaluate and/or compare the measured transmission projection data against. In the blank run, the scanner is used to perform a transmission scan without the subject present therein such that a blank set of transmission projection data is collected. In a preferred embodiment, this data is stored in a reference memory 120.

In preparation for the first iteration of the reconstruction process, an attenuation map memory 130 and an image memory 140 are initialized by loading them with assumed or first estimates of the attenuation map and emission map respectively. The first estimate for the attenuation map is optionally characterized by a uniform attenuation value inside a predetermined contour which contains the subject and zero outside the contour. Likewise, the first estimate for the emission map is optionally characterized by a uniform value inside the contour and zero outside. Alternately, the availability of additional a priori information allows for more accurate first estimates.

With each iteration of the reconstruction process, a first projector 150 reprojects and/or forward projects the estimated emission map stored in the image memory 140 to obtain projection views thereof. Likewise, a second projector 152 reprojects and/or forward projects the attenuation map stored in the attenuation map memory 130 to obtain projection views thereof. The projections are performed using multi-dimensional projection models. That is to say, the multi-dimensional projection models account for radiation from multiple directions, as opposed to merely linear models that only account for radiation traveling along a singular direction. In a preferred embodiment, the projection models account for any one or more of the following: scatter, the geometric point response (resolution) associated with the imaging apparatus, randomness corrections which account for random simultaneous photon detection not resulting from the same annihilation event in PET applications, and/or cross-talk due to changing photon energies. In at least one embodiment, the projection models used by the first and second projectors 150 and 152 are not the same. Alternately, for some applications, identical projection models are employed.

A first data processor 160 updates the attenuation maps in the attenuation map memory 130 with each iteration, and a second data processor 170 updates the emission maps in the image memory 140 with each iteration.

The first data processor 160 recalculates the attenuation map by taking a previously stored attenuation map from the attenuation map memory 130 and adjusting it based upon a number of factors. The factors include: (i) the measured emission projection data from the emission memory 112; and, (ii) a reprojection of the previous emission map stored in the image memory 140 which is reprojected via the projector 150. More specifically, the first data processor 160 samples the emission memory 112 and the output projection views from the projector 150 to complete each update of the attenuation map which is then reloaded into the attenuation map memory 130. In a preferred embodiment, employing so called source-assisted reconstruction, in addition to the above, measured transmission projection data is also incorporated with each update of the attenuation map. That is to say, the measured transmission projections are also sampled from the transmission memory 114 by the first data processor 160 for each update or recalculation. In addition, baseline or reference transmission projections from the reference memory 120 are also taken into account. A detailed account of the first data processor's operation is given below in more mathematical terms.

In source-assisted reconstruction, the second data processor 170 updates the emission map based on the following factors: (i) the measured emission projection data; (ii) a reprojection of the previous emission map; and, (iii) a reprojection of the attenuation map. More specifically, with each iteration, the second data processor 170 samples the emission memory 112, the first projector 150, and the second projector 152. Based upon the data collected, the second data processor 170 recalculates the emission map and reloads the updated emission map back into the image memory 140. Again, a detailed account of the second data processor's operation is given below in more mathematical terms.

Upon completion of the final iteration, a video processor 300 extracts or otherwise receives data from the image memory 140 which represents a reconstruction of the radionuclide distribution within the region of interest. The video processor 300 then formats it into image representations of the subject for viewing on a human-viewable display, such as a video monitor 310 or other appropriate rendering device.

In more mathematical terms, the operation of the image processor 100 is as follows. The iterative ML-EM reconstruction is an iterative solver for a linear system of equations. It has a robustness in reconstruction that is difficult for other reconstruction techniques to achieve, based on the solution of linear systems. An important feature of the ML-EM algorithm is that given certain mild restrictions appropriate for nuclear medicine emission imaging, it is applicable to any linear system of equations, whether it be over- or under-determined, consistent or inconsistent. In any event, after a number of iterations, the ML-EM algorithm converges to a solution that is the most likely or the most probable, given the original data.

One of the appealing qualities of this iterative algorithm is that a general probability model of detection is used. The underlying radionuclide distribution is continuous, but the signal or projection is detected at a discrete number of bins, or sampling locations. In what follows, $P_i$ represents the total detected photons in the $i^{th}$ detector location (i.e., the measured emission projection data). There are M detector locations. Also, the radionuclide distribution is represented as a discrete collection of basis functions. The basis function for the emission distribution is the voxel. $F_k$ represent the average of the continuous radionuclide distribution over the kth image voxel. There are K image voxels. The transfer matrix coefficient $m_{ki}$ (i.e., the projection model) is the probability that a photon emitted in voxel k per unit time is detected in detector location i. As each measurement can be noisy, the noise associated with each measurement is denoted by $n_i$. Generally however, enough is known about the imaging system to be able to accurately model the statistical properties of the noise. Hence, the total photon count at the $i^{th}$ detector location is the sum of all voxels contributing to that detector location. This is mathematically expressed as:

$$P_i = \Delta t_i \sum_{k=1}^{K} F_k m_{ki} + n_i, \quad (1)$$
$$i = 1, \ldots, M,$$

where $\Delta t_i$ is the imaging time for the $i^{th}$ projection.

This linear system of equations is then the basic imaging model. Denoting $f_k^{(h)}$ (i.e., the $k^{th}$ voxel of the emission map) as the estimate of the activity $F_k$ in voxel k on the $h^{th}$ iteration of the ML-EM reconstruction, the ML-EM estimate for the (h+1)-iteration is given by:

$$f_k^{(h+1)} = f_k^{(h)} \frac{1}{\sum_{i=1}^{M} m_{ki}} \sum_{i=1}^{M} \frac{P_i}{\Delta t_i \sum_{n=1}^{K} f_n^{(h)} m_{ni}} m_{ki}. \quad (2)$$

With this method scatter, resolution, and attenuation can be incorporated into the model $m_{ki}$. However, the inclusion of attenuation and scatter in the transfer matrix employs a priori knowledge of the attenuation map.

In a sourceless reconstruction for PET data, the lack of an attenuation map for emission imaging leads to a formulation that includes an unknown attenuation map. The forward problem is stated as:

$$P_i = \Delta t_i \sum_{k=1}^{K} m_{ki} F_k \exp\left(-\sum_{j \in N_{ki}} c_{ji} \mu_j\right) + n_i, \quad (3)$$
$$i = 1, \ldots, M,$$

where $\mu_j$ is the linear attenuation coefficient of the $j^{th}$ pixel of the attenuation map, and $c_{ji}$ is the effective attenuation length of $\mu_j$. The set of pixels $N_{ki}$ is given by: $N_{ki}=\{\text{pixel } j | m_{ji} \neq 0, \text{ for source-detector pair } (F_k, P_i)\}$. Geometrically, the set $N_{ki}$ is the set of pixels intersecting and covering the line of response i that contains the source pixel k. The estimate $(f_k, u_j)$ of the unknowns $(F_k, \mu_j)$ is given by:

$$f_k^{(h+1)} = f_k^{(h)} \frac{1}{\sum_i \exp\left(-\sum_{j=0}^{N_{\mu}-1} u_j^{(h)} c_{ji}\right) m_{ki}} \sum_i \frac{P_i m_{ki}}{\Delta t_i \sum_n f_n^{(h)} m_{ni}}, \quad (4)$$

for the emission map; and, $$u_j^{(h+1)} = u_j^{(h)} \frac{\sum_i \exp\left(-\sum_j u_j^{(h)} c_{ji}\right) c_{ji} \sum_s f_s^{(h)} m_{si}}{\sum_i P_i c_{ji}}, \quad (5)$$

for the attenuation map.

However, source-assisted reconstruction utilizes the measured transmission data, represented by $T_n$, and blank scan, represented by $E_n$, to stabilize the sourceless reconstruction. It accomplishes this by incorporating the transmission scan as a priori information in the likelihood probability function. The result is a different update for the transmission map. Accordingly, for PET, the transmission update is now given by:

$$\mu_j^{(h+1)} = \mu_j^{(h)} * \frac{\sum_i P_i c_{ji} + \sum_n T_n \hat{c}_{jn}}{\Delta t_i \sum_{i,k} \exp\left(-\sum_j \mu_j^{(h)} c_{ji}\right) c_{ji} f_k^{(h)} m_{ki} + \Delta_n \sum_n \exp\left(-\sum_j \mu_j^{(h)} \hat{c}_{jn}\right) \hat{c}_{jn} E_n}, \quad (6)$$

in which $\Delta t_i$ is the scan time per projection for the emission data, and $\Delta_n$ is a normalization constant that reflects the ratio of the emission scan-time to the transmission scan time. The coefficients $\hat{c}_{jn}$ measure the contribution of the $j^{th}$ voxel of the attenuation map to the $n^{th}$ transmission measurement and are not always the same as the coefficients $c_{ji}$ defined above. They depend on the particular embodiment of the scanner employed.

Therefore, in source-assisted reconstruction with PET data, the second data processor 170 and the first data processor 160 carry out the former and later computations from equations (4) and (6), respectively, to update the emission and attenuation maps.

In a sourceless reconstruction for SPECT data, a similar set of algorithms is developed. The forward problem in this case is again:

$$P_i = \Delta t_i \sum_{k=1}^{K} m_{ki} F_k \exp\left(-\sum_{j \in N_{ki}} c_{ji} \mu_j\right) + n_i, \quad (7)$$

$$i = 1, \ldots, M.$$

Figure 7:
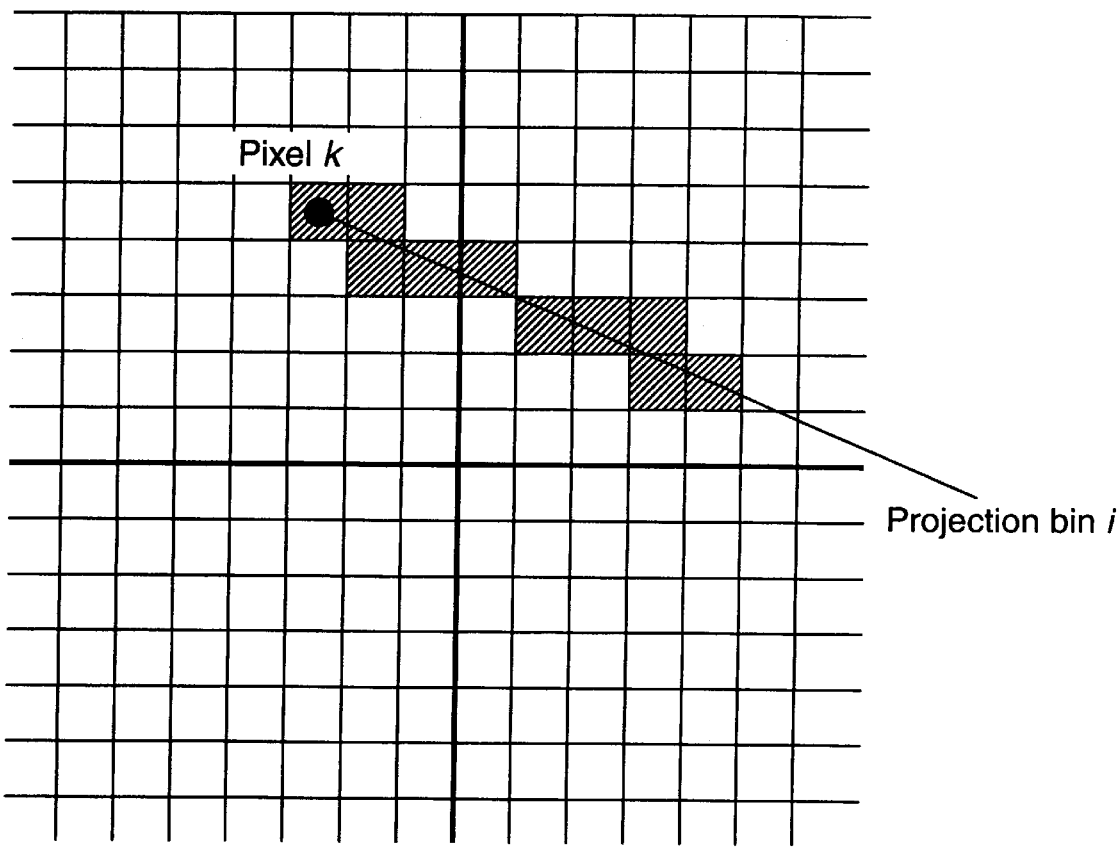

However, for SPECT, the set $N_{ki}$ is defined differently as illustrated in FIG. 7. The set $N_{ki}$ is the set of pixels that cover the attenuation line integral from the source pixel k to the projection bin I. This leads to a variation of the algorithm. In this embodiment, the emission update is given by:

$$f_k^{(h+1)} = f_k^{(h)} * \frac{1}{\sum_i \exp\left(-\sum_{j \in N_{ki}} \mu_j^{(h)} c_{ji}\right) m_{ki}} \sum_i \frac{P_i m_{ki} \exp\left(-\sum_{j \in N_{ki}} \mu_j^{(h)} c_{ji}\right)}{\Delta t_i \sum_n \exp\left(-\sum_{j \in N_{ni}} \mu_j^{(h)} c_{ji}\right) f_n^{(h)} m_{ni}}; \quad (8)$$

and, the transmission image update is given by:

$$\mu_j^{(h+1)} = \mu_j^{(h)} * \frac{\sum_i \left\{ \frac{P_i}{\sum_n \exp\left(-\sum_{(j,i) \in N_{ai}} \mu_j^{(h)} c_{ji}\right) f_n^{(h)} m_{ni}} \sum_k \exp\left(-\sum_{(j,i) \in N_{ki}} \mu_j^{(h)} c_{ji}\right) f_k^{(h)} m_{ki} \begin{cases} 0, & (j,i) \notin N_{ki} \\ c_{ji}, & (j,i) \in N_{ki} \end{cases} \right\}}{\sum_{i,k} \left\{ c_{ji} \exp\left(-\sum_{j \in N_{ki}} \mu_j^{(h)} c_{ji}\right) f_k^{(h)} m_{ki} \begin{cases} 0, & j \notin N_{ki} \\ 1, & j \in N_{ki} \end{cases} \right\}}. \quad (9)$$

The update rule for the emission map in source-assisted SPECT is the same as the update rule for sourceless SPECT. However, the transmission map update rule is changed to the following:

$$\mu_j^{(h+1)} = \mu_j^{(h)} * \frac{\sum_i \left\{ \frac{P_i}{\sum_n \exp\left(-\sum_{(j,i) \in N_{ai}} \mu_j^{(h)} c_{ji}\right) f_n^{(h)} m_{ni}} \sum_k \exp\left(-\sum_{(j,i) \in N_{ki}} \mu_j^{(h)} c_{ji}\right) f_k^{(h)} m_{ki} \begin{cases} 0, & (j,i) \notin N_{ki} \\ c_{ji}, & (j,i) \in N_{ki} \end{cases} \right\} + \sum_n T_n \hat{c}_{jn}}{\sum_{i,k} \left\{ c_{ji} \exp\left(-\sum_{j \in N_{ki}} \mu_j^{(h)} c_{ji}\right) f_k^{(h)} m_{ki} \begin{cases} 0, & j \notin N_{ki} \\ 1, & j \in N_{ki} \end{cases} \right\} + \Delta_n \sum_n \exp\left(-\sum_j \mu_j^{(h)} \hat{c}_{jn}\right) \hat{c}_{jn} E_n}. \quad (10)$$

Accordingly, in source-assisted reconstruction with SPECT data, the second data processor 170 and the first data processor 160 carry out the former and later computations from equations (8) and (10), respectively, to update the emission and attenuation maps.

Optionally, the operations of the first and second data processors 160 and 170, as well as the other components, are implemented as hardware, software, or combinations of hardware and software configurations.

In any event, the invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method of ML-EM image reconstruction for use in connection with a diagnostic imaging apparatus that generates projection data comprising:
   (a) collecting projection data including measured emission projection data and measured transmission projection data, wherein said measured transmission projection data is truncated;
   (b) assuming an initial emission map;
   (c) assuming an initial attenuation map;
   (d) iteratively updating the emission map and the attenuation map;
   (e) with each iteration, recalculating the emission map by taking a previous emission map and adjusting it based upon: (i) the measured emission projection data; (ii) a reprojection of the previous emission map which is carried out with a multi-dimensional projection model; and, (iii) a reprojection of the attenuation map; and,
   (f) with each iteration, recalculating the attenuation map by taking a previous attenuation map and adjusting it based upon: (i) the measured emission projection data; (ii) the reprojection of the previous emission map which is carried out with the multi-dimensional projection model; and (iii) the measured transmission projection data.

2. The method according to claim 1, wherein the diagnostic imaging apparatus is selected from a group consisting of PET scanners and SPECT scanners.

3. The method according to claim 2, wherein the multi-dimensional projection model includes one or more of the following: scatter corrections, random corrections, geometric point response corrections, and cross-talk corrections.

4. The method according to claim 1, wherein the step of collecting projection data further includes collecting a blank set of transmission projection data which is collected without a subject present in the diagnostic imaging apparatus.

5. The method according to claim 4, wherein the adjustment to the previous attenuation map in the recalculating step is also made based upon the blank set of transmission projection data.

6. A medical diagnostic imaging apparatus for reconstructing image representations of a subject being examined therewith comprising:
   an emission memory which stores measured emission projection data from the subject;
   a transmission memory which stores measured transmission projection data from the subject, wherein said transmission projection data is truncated;
   an image memory which stores emission maps;
   an attenuation map memory which stores attenuation maps;
   a first projector which generates emission map projections via forward projection of the emission maps from the image memory, said projector using a first multi-dimensional projection model;
   a second projector which generates attenuation map projections via forward projection of the attenuation maps from the attenuation map memory, said projector using a second multi-dimensional projection model;
   a first data processor which samples the emission memory, the transmission memory, and the first projector, and in accordance therewith updates the attenuation maps stored in the attenuation map memory;
   a second data processor which samples the emission memory, the first projector, and the second projector, and in accordance therewith updates the emission maps stored in the image memory; and,
   a human-viewable display which renders reconstructed images representations of the subject from the emission maps.

7. The medical diagnostic imaging apparatus according to claim 6, further comprising:
   a scanner selected from a group consisting of a SPECT scanner and a PET scanner, said scanner being employed to collect the emission projection data and transmission projection data from the subject.

8. The medical diagnostic imaging apparatus according to claim 7, further comprising:
   a reference memory which stores transmission projection data from a blank scanner run performed without the subject present in the scanner.

9. The medical diagnostic imaging apparatus according to claim 8, wherein the first data processor also samples the reference memory when it updates the attenuation maps stored in the attenuation map memory, such that the update is also made in accordance therewith.

10. The medical diagnostic imaging apparatus according to claim 6, wherein the updates made by the first and second data processors are iterative.

11. The medical diagnostic imaging apparatus according to claim 6, wherein the first and second projection models are not the same.

12. The medical diagnostic imaging apparatus according to claim 6, wherein the first and second projection models are the same.

13. A method of reconstructing an image for use in connection with a nuclear imaging apparatus, said method comprising:
   (a) collecting emission projection data;
   (b) collecting truncated transmission projection data;
   (c) updating an attenuation map in accordance with the collected transmission projection data, the collected emission projection data, and a reprojection of an emission map; and,
   (d) updating the emission map in accordance with the collected emission projection data, the reprojection of the preceding emission map, and a reprojection of the attenuation map.

14. The method according to claim 13, wherein steps (c) and (d) are repeated until the updated emission map is within a desired tolerance of the preceding emission map.

15. The method according the claim 13, wherein projection models used in reprojecting emission and transmission maps in steps (c) and (d) are multi-dimensional.

16. The method of claim 1, wherein the assumed initial attenuation map is selected from:
   a uniform nonzero attenuation value inside a predetermined contour which contains the subject and a value of zero outside the contour; and
   an attenuation map based on a priori knowledge of the attenuation map.

17. The method of claim 16, wherein the assumed initial emission map is selected from:
   a uniform nonzero value inside a predetermined contour which contains the subject and a value of zero outside the contour; and
   an emission map based on a priori knowledge of the emission map.

18. A method of ML-EM reconstruction for use in connection with a diagnostic imaging apparatus, the method comprising:
   (a) collecting truncated transmission projection data;
   (b) estimating an attenuation map;
   (c) estimating an emission map;
   (d) collecting emission projection data;
   (e) adjusting the emission map using:
      (i) the collected emission projection data;
      (ii) a reprojection of a previous emission map which is carried out with a multi-dimensional projection model; and
      (iii) a reprojection of the attenuation map;
   (f) adjusting the attenuation map using a combination of:
      (i) the collected emission projection data;
      (ii) a reprojection of a previous emission map which is carried out with a multi-dimensional projection model; and
      (iii) the collected truncated transmission projection data;
   (g) iteratively repeating steps (e) and (f) until an emission map and attenuation map are reconstructed which optimize a likelihood probability function.

19. The method according to claim 18, wherein the transmission projection data includes a blank set of transmission projection data collected without a subject present in the diagnostic imaging apparatus.

20. A medical diagnostic imaging apparatus for reconstructing image representations of a subject being examined therewith comprising:
   an emission memory which stores measured emission projection data from the subject;
   a transmission memory which stores measured transmission projection data from the subject, wherein the transmission projection data is truncated, and wherein the transmission projection data is further characterized by one or both of noise and poor statistical quality;
   an image memory which stores emission maps;
   an attenuation map memory which stores attenuation maps;
   a first projector which generates emission map projections via forward projection of the emission maps from the image memory, said projector using a first multi-dimensional projection model;
   a second projector which generates attenuation map projections via forward projection of the attenuation maps from the attenuation map memory, said projector using a second multi-dimensional projection model;
   a first data processor which samples the emission memory, the transmission memory, and the first projector, and in accordance therewith updates the attenuation maps stored in the attenuation map memory;
   a second data processor which samples the emission memory, the first projector, and the second projector, and in accordance therewith updates the emission maps stored in the image memory; and,
   a human-viewable display which renders reconstructed images representations of the subject from the emission maps.

21. The medical diagnostic imaging apparatus according to claim 16, wherein the updates made by the first and second data processors iteratively optimize a likelihood probability function.

* * * * *